US008939580B2

(12) United States Patent
Nakajima et al.

(10) Patent No.: US 8,939,580 B2
(45) Date of Patent: Jan. 27, 2015

(54) CHARACTERISTIC IMAGE EXTRACTION METHOD AND OPHTHALMOLOGIC APPARATUS

(75) Inventors: Junko Nakajima, Tokyo (JP); Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 278 days.

(21) Appl. No.: 13/074,203

(22) Filed: Mar. 29, 2011

(65) Prior Publication Data

US 2011/0267580 A1    Nov. 3, 2011

(30) Foreign Application Priority Data

Apr. 30, 2010    (JP) .................................. 2010-105402

(51) Int. Cl.
| | |
|---|---|
| *A61B 3/14* | (2006.01) |
| *A61B 3/10* | (2006.01) |
| *G06T 7/00* | (2006.01) |
| *G06K 9/00* | (2006.01) |
| *A61B 3/00* | (2006.01) |

(52) U.S. Cl.
CPC .......... *G06T 7/0081* (2013.01); *G06K 9/00597* (2013.01); *A61B 3/0091* (2013.01); *A61B 3/102* (2013.01); *A61B 3/1025* (2013.01); *G06T 2207/30041* (2013.01)
USPC ............ 351/206; 351/209; 351/211; 351/246

(58) Field of Classification Search
USPC ................................................. 351/206, 211
See application file for complete search history.

(56) References Cited

U.S. PATENT DOCUMENTS

| 7,566,132 B2 | 7/2009 | Fukuma et al. |
| 7,639,845 B2 | 12/2009 | Utsunomiya |
| 8,079,708 B2 * | 12/2011 | Hamaguchi et al. .......... 351/205 |
| 8,118,430 B2 * | 2/2012 | Ono et al. ...................... 351/206 |

(Continued)

FOREIGN PATENT DOCUMENTS

| CN | 101049230 A | 10/2007 |
| EP | 1842483 A1 | 10/2007 |

(Continued)

OTHER PUBLICATIONS

Communication dated Sep. 5, 2011, forwarding a European Search Report dated Aug. 29, 2011, in European Application No. 11162537. 2-2319.
Hideo Kawai et al., Eye Movement Analysis System Using Fundus Images, Pattern Recognition, Elsevier, GB, vol. 19, No. 1, Jan. 1, 1986, pp. 77-84.

(Continued)

*Primary Examiner* — Jordan Schwartz
(74) *Attorney, Agent, or Firm* — Fitzpatrick, Cella, Harper & Scinto (57) ABSTRACT

Provided is an ophthalmologic apparatus for detecting an eye movement from movements of a plurality of characteristic points within a fundus image. It is determined whether or not the plurality of characteristic points are included in a new fundus image when a position of a fixation index is changed, based on a relationship between a displacement amount of the fixation index and positions of the characteristic points within a fundus plane. If it is determined that at least one of the plurality of characteristic points is not included in the new fundus image, new characteristic points are extracted from a limited range within a new fundus plane image. Accordingly, the characteristic points can be efficiently reacquired for eye movement detection performed when an imaging target region of an eye to be inspected is changed by the fixation index.

33 Claims, 4 Drawing Sheets

(56) References Cited

U.S. PATENT DOCUMENTS

| | | | |
|---|---|---|---|
| 2003/0223037 A1* | 12/2003 | Chernyak | 351/209 |
| 2005/0281440 A1 | 12/2005 | Pemer | |
| 2007/0236660 A1 | 10/2007 | Fukuma et al. | |
| 2010/0039616 A1* | 2/2010 | Yumikake et al. | 351/206 |
| 2010/0182610 A1 | 7/2010 | Utsunomiya | |
| 2010/0182612 A1 | 7/2010 | Yoshida et al. | |
| 2011/0032479 A1 | 2/2011 | Utsunomiya | |

FOREIGN PATENT DOCUMENTS

| | | |
|---|---|---|
| JP | 10-295645 A | 11/1998 |
| JP | 3708669 B2 | 10/2005 |

OTHER PUBLICATIONS

Mar. 19, 2013 Chinese Official Action in Chinese Patent Appln. No. 20110107454.5.

* cited by examiner

CHARACTERISTIC IMAGE EXTRACTION METHOD AND OPHTHALMOLOGIC APPARATUS

BACKGROUND OF THE INVENTION

1. Field of the Invention

The present invention relates to a characteristic image extraction method and an ophthalmologic apparatus, in particular, a characteristic image extraction method and an ophthalmologic apparatus which involve a devised tracking function working when a fixation index is moved.

2. Description of the Related Art

At present, various optical equipments are used as ophthalmologic apparatuses or ophthalmic equipments. Of those, used as an optical equipment for observing an eye are various equipments including an anterior ocular segment photographing device, a fundus camera, a confocal scanning laser ophthalmoscope (SLO), and an optical coherence tomography (OCT) apparatus that is an optical tomographic imaging apparatus using optical interference due to low coherence light. In particular, the OCT apparatus using the optical interference due to the low coherence light is an apparatus for obtaining a tomographic image of a fundus with high resolution, and is currently on the way to becoming an indispensable apparatus in outpatient clinics specialized in retinas.

The OCT apparatus is an apparatus for applying low coherence light to a sample represented by a retina and measuring reflected light from the sample with high sensitivity by using an interferometer. Further, the OCT apparatus can obtain a tomographic image by scanning the low coherence light over the sample. In particular, the tomographic image of a retina is widely used in ophthalmic diagnosis.

In recent years, the OCT apparatuses conventionally of a so-called time domain method, in which a tomographic image is acquired by performing scanning along an optical path length of a reference beam in each tomographic acquisition position, have made a shift to OCT apparatuses of a Fourier domain method that eliminates the need for the scanning along the optical path length of the reference beam in each tomographic acquisition position. Therefore, it is now possible to acquire the tomographic image with faster speed than before. The increase in the speed allows three-dimensional image taking of the fundus, which has been difficult with the time domain method, to be carried out.

However, in the three-dimensional image taking, two-dimensional scanning of the fundus is necessary even with the Fourier domain method, and hence an influence of an involuntary eye movement of an eye to be inspected cannot be ignored. The influence of the eye movement can be reduced by detecting the eye movement at the time of image taking and correcting a low coherence light beam scanned over the retina in synchronization with the detected eye movement. The detection of the eye movement can be realized by taking a fundus image in parallel with the image taking performed by the OCT apparatus and detecting displacements of characteristic points within the fundus image.

Further, in some of the ophthalmologic apparatuses or ophthalmic equipments, in particular, equipments for taking a fundus image, an image is in some cases acquired by greatly changing a fixation point of the eye to be inspected according to an imaging target region of the eye to be inspected. A fixation index or a fixation lamp is used to change the fixation point of the eye to be inspected. Also in the OCT apparatus, when a photographing position is to be greatly changed, the fixation point of the eye to be inspected is caused to change by moving the fixation index. This greatly changes a range of the fundus that can be observed through a pupil. By appropriately changing the position of the fixation index, the imaging target region can be guided to a position that can be observed.

Japanese Patent No. 3,708,669 discloses a fundus imaging apparatus configured as follows. That is, when the fixation index is moved in order to change the imaging target region during the taking of the fundus image, a relationship between an optical axis and a pupil position is changed simultaneously. According to the change, the optical axis is automatically adjusted so as to be the center of the pupil.

Japanese Patent No. 3,708,669 discloses automatic adjustment of the change in the relationship between the optical axis and the pupil position, which becomes a problem when a photographing target region is changed by performing guidance with the fixation index.

However, there is no description regarding the characteristic points within the fundus image being used to detect the eye movement. For the fundus imaging apparatus having such a function, nothing is taken into consideration regarding the problem that a region that can be observed changes according to the movement of the fixation index and the characteristic points within the fundus image are displaced from the region that can be observed.

SUMMARY OF THE INVENTION

The present invention has been made in view of the above-mentioned situations, and an object thereof is to alleviate inefficiency exhibited at a time of reacquiring characteristic points for eye movement detection when an imaging target region of an eye to be inspected is changed due to a movement of a fixation index. In other words, the object of the present invention is to provide a method of efficiently extracting and acquiring a plurality of characteristic points described above and an ophthalmologic apparatus using the method. Note that, in the present invention, the characteristic points can be understood as characteristic images.

In order to solve the above-mentioned problem, according to the present invention, there is provided an ophthalmologic apparatus for extracting a plurality of characteristic images from a fundus image of an eye to be inspected including a fixation index presenting unit for presenting a fixation index, an extracting unit for extracting, when a presentation position of the fixation index is changed by the fixation index presenting unit, the characteristic images from a range based on the changed presentation position within the acquired fundus image of the eye to be inspected, and a determining unit for determining whether or not each of the plurality of characteristic images is included in a new fundus image.

Further, according to the present invention, there is provided a characteristic image extraction method for extracting a plurality of characteristic images from a fundus image of an eye to be inspected in order to detect a movement of the eye to be inspected, the characteristic image extraction method including the steps of determining whether or not the plurality of characteristic images are included in a new fundus image of the eye to be inspected when a position of a fixation index is changed, setting a range for extracting new characteristic images in the new fundus image if it is determined that at least one of the plurality of characteristic images is not included in the new fundus image, and extracting the new characteristic images from the range set in the new fundus image.

According to the present invention, a time period required to acquire new characteristic points can be shortened in a case where characteristic points used for the eye movement detection are displaced from an imaging area when the imaging target region of the eye to be inspected is changed due to the movement of the fixation index.

Further features of the present invention will become apparent from the following description of exemplary embodiments with reference to the attached drawings.

DESCRIPTION OF THE EMBODIMENTS

Hereinafter, embodiments of the present invention are described in detail with reference to the attached drawings.

First Embodiment

Figure 2:
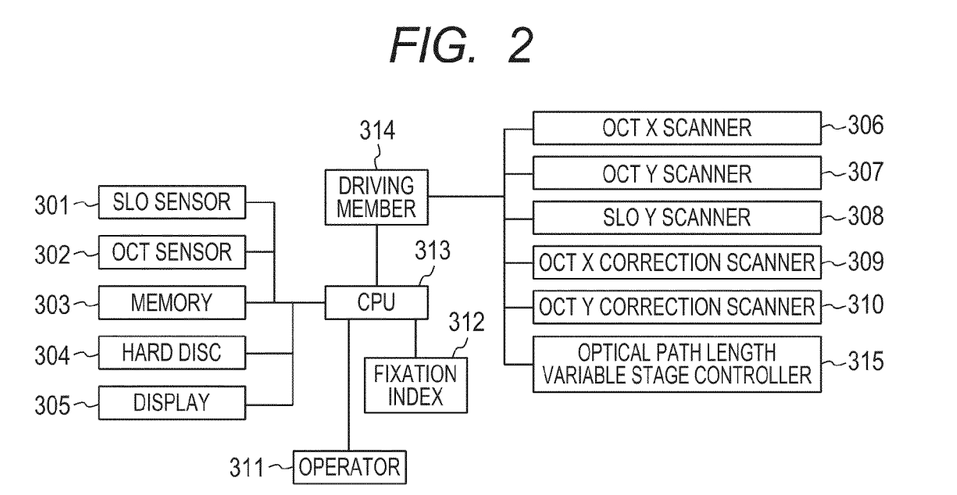
FIG. 2 is a block diagram of a control part of the OCT apparatus with a tracking function using a line-scan SLO.
Figure 3:
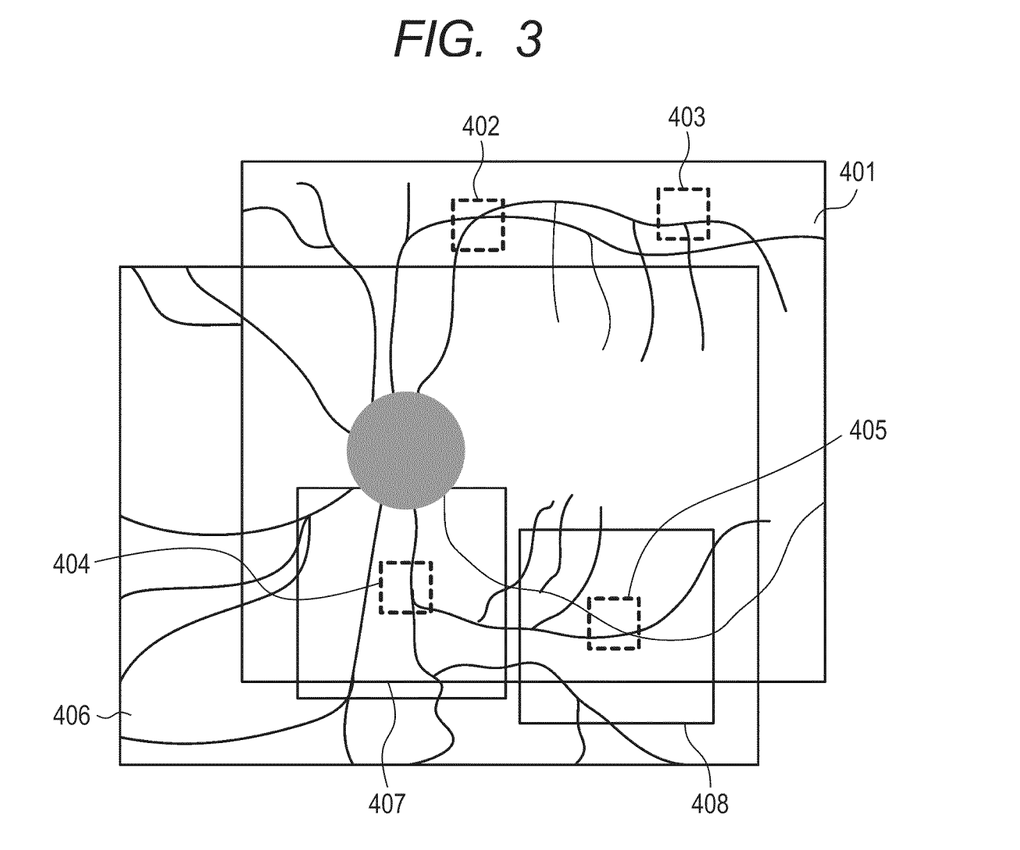
FIG. 3 is a conceptual diagram illustrating a relationship between SLO images and templates according to a first embodiment of the present invention.
Figure 4:
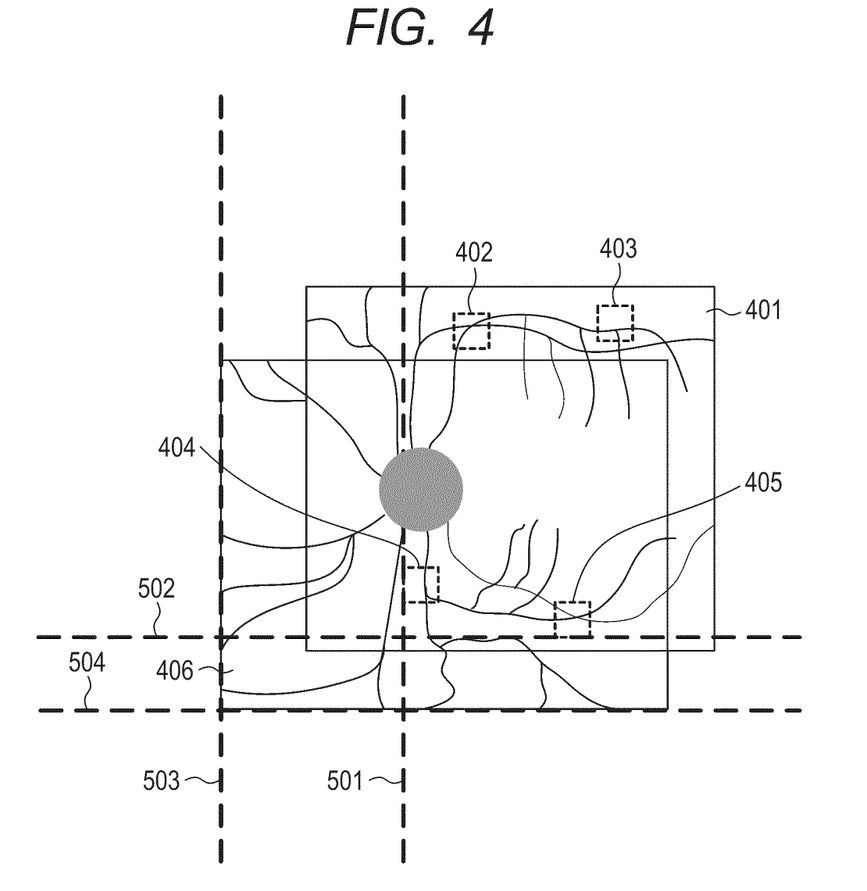
FIG. 4 is a conceptual diagram illustrating a relationship between the SLO images and the templates according to a second embodiment of the present invention.

A first embodiment is described by taking a case where the present invention is applied to an OCT apparatus with a tracking function for extracting templates (also referred to as "first characteristic points or first characteristic images") from a fundus image (also referred to as "first fundus image"), subjecting a newly (continuously) taken fundus image (also referred to as "second fundus image") to pattern matching (retrieving the extracted characteristic images from the newly taken fundus image) to thereby detect an eye movement, and correcting an OCT beam. The description is made with reference to an optical structure diagram of FIG. 1 illustrating the OCT apparatus with a tracking function using a line-scan SLO, a block diagram of FIG. 2 illustrating the OCT apparatus with a tracking function using a line-scan SLO, and diagrams of FIGS. 3 and 4 illustrating fundus images.

In a tracking technology performed in this embodiment, a movement in a direction along a fundus plane is detected by continuously taking the fundus image simultaneously with an OCT image, and image-taking is performed by changing a position of the OCT beam so as to follow the eye movement. The fundus image referred to here may be any image as long as a plane image of the fundus is taken in two or more dimensions by collective fundus image taking, a point-scan SLO, a line-scan SLO, OCT C-scan, or the like.

Hereinafter, the first embodiment of the present invention is described.

Figure 1:
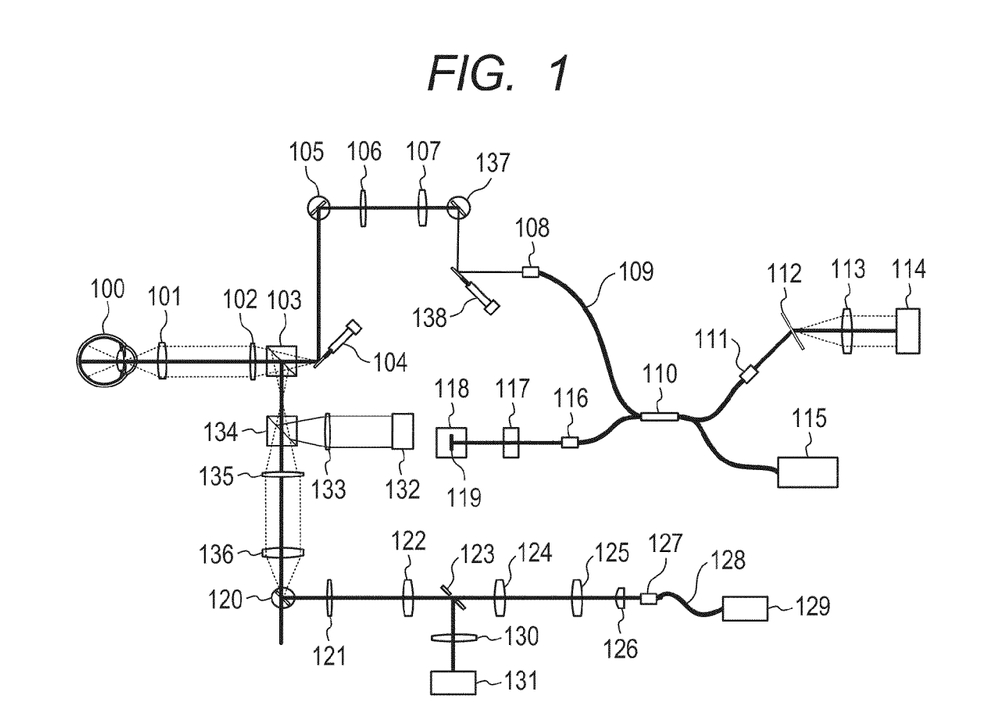
FIG. 1 is an optical structure diagram of an OCT apparatus with a tracking function using a line-scan SLO according to embodiments of the present invention.

FIG. 1 is the optical structure diagram of the OCT apparatus with a tracking function using a line-scan SLO. Of the OCT apparatus illustrated in FIG. 1, an SLO part is first described.

First, a beam emitted from a laser light source 129 passes through an optical fiber 128 and enters a fiber collimator 127 to become a collimated beam. The beam that has become the collimated beam enters a cylindrical lens 126 and spreads in a line shape. After that, the beam passes through relay lenses 124 and 125 and passes through a hole formed in a central part of a ring mirror 123. After that, the beam passes through relay lenses 121 and 122 and is deflected toward a predetermined direction by an SLO Y scanner 120.

After that, the beam passes through relay lenses 135 and 136 and passes through a dichroic beam splitter 134 to travel toward a dichroic beam splitter 103. After that, the beam passes through relay lenses 101 and 102 to enter an eye 100 to be inspected and forms an image on the fundus of the eye 100 to be inspected in a line shape.

Subsequently, the beam scattered by the fundus is collected. The beam scattered by the fundus exits from the eye 100 to be inspected, passes through the relay lenses 101 and 102, and is separated from a scattered OCT beam from the fundus, which is described later, by the dichroic beam splitter 103. After that, the beam is separated from a beam of a fixation index, which is described later, by the dichroic beam splitter 134, passes through the relay lenses 135 and 136, and is reflected by the SLO Y scanner 120. After that, the beam passes through the relay lenses 121 and 122 and is reflected by the ring mirror 123 being a mirror having a ring shape. The beam reflected by the ring mirror 123 passes through a lens 130 and is detected by a line sensor 131.

Intensity information on the beam detected by the line sensor 131 is converted into a digital signal, sent to a CPU 313 of FIG. 2, and processed by the CPU 313 to thereby become a two-dimensional fundus image. The two-dimensional fundus image is saved to a memory 303 or a hard disk 304 and displayed on a display 305 to allow an operator 311 to see the two-dimensional fundus image.

Next described is an OCT part of the OCT apparatus illustrated in FIG. 1.

The beam emitted from a low coherence light source 115 passes through a fiber and enters a fiber coupler 110 to be branched into two beams in proportions according to the type of coupler. The two beams obtained after the branching are respectively referred to as "reference beam" and "measuring beam".

The reference beam passes through a fiber collimator 116 to exit to the outside, then passes through dispersion compensating glass 117, and is reflected by a reference mirror 119. The reference mirror 119 is fixed to an optical path length variable stage (OCT stage) 118 for changing an optical path length of the reference beam. The reflected reference beam follows the above-mentioned path in the reverse direction to return to the fiber coupler 110.

The measuring beam passes through an optical fiber 109 and reaches a fiber collimator 108 to exit from the fiber collimator 108 to the outside. The measuring beam is reflected by an OCT X correction scanner 138 and then by an OCT Y correction scanner 137 toward a predetermined direction. After that, the measuring beam passes through relay lenses 106 and 107 and is reflected by an OCT Y scanner 105 and an OCT X scanner 104 toward a predetermined direction. The reflected measuring beam passes through the dichroic beam splitter 103 and through the relay lenses 101 and 102 to enter the eye 100 to be inspected and forms a punctiform image on the fundus of the eye 100 to be inspected in a spot shape. The return beam from the fundus of the eye 100 to be inspected follows the above-mentioned path in the reverse direction to return to the fiber coupler 110.

The measuring beam and the reference beam that have returned to the fiber coupler 110 are combined with each other at the fiber coupler 110 to cause interference. The interfered beam exits from a fiber collimator 111 to be dispersed by a transmission grating 112, passes through a lens 113, and is received by a line sensor 114. Intensity information on the beam received by the line sensor 114 is sent to the CPU 313 of FIG. 2 as a digital signal and subjected to a signal processing by the CPU 313 to become a two-dimensional tomographic image. The two-dimensional tomographic image of an eye to be inspected is saved to the memory 303 or the hard disk 304 of FIG. 2. Further, the two-dimensional tomographic image of the eye to be inspected can be displayed on the display 305, which allows the operator 311 to see the two-dimensional tomographic image of the eye to be inspected. Note that, the above-mentioned optical system functions as a tomographic image acquiring unit by further including the line sensor 114 and the CPU 313.

A fixation index display part 132 being a fixation index presenting unit is located in a position conjugated with the fundus. The beam emitted from the fixation index display part 132 passes through a lens 133 and the dichroic beam splitter 134 to travel toward the dichroic beam splitter 103. After that, the beam passes through the relay lenses (101 and 102) and forms an image on the fundus. It is possible to take a two-dimensional image of the fundus in a desired position thereof by fixing a line of sight of the eye to be inspected to the fixation index displayed in the fixation index display part 132, and the position for image taking is changed by changing a display position of the fixation index.

Figure 5:
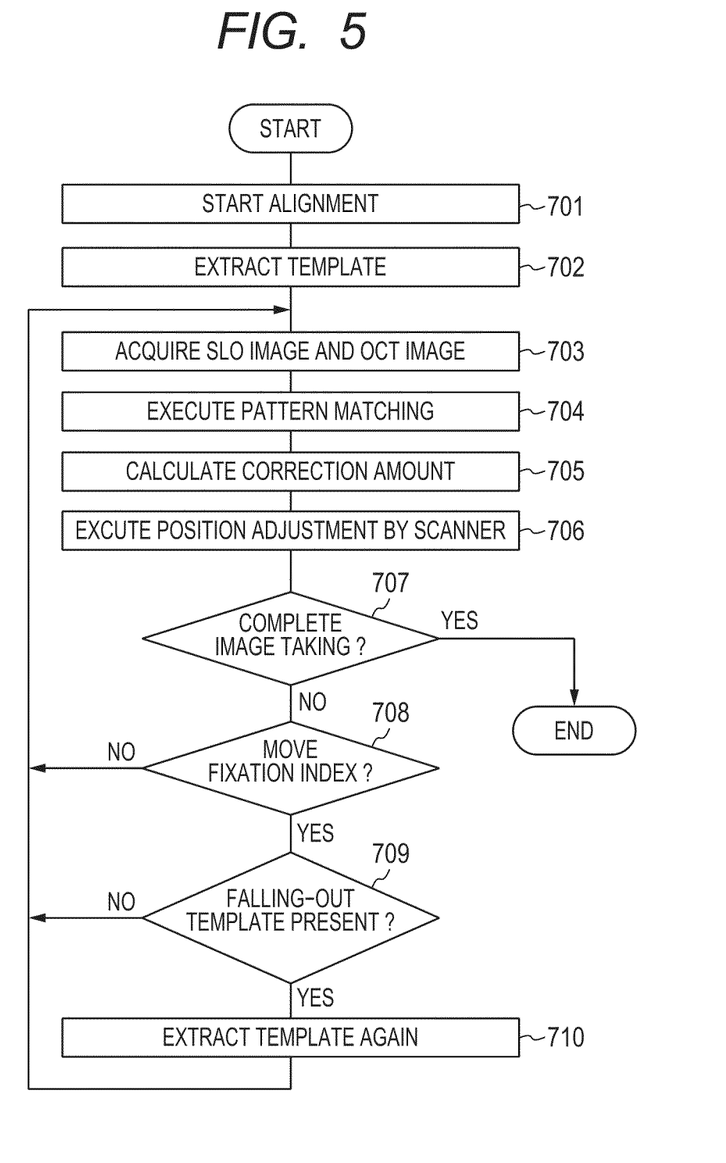
FIG. 5 is a flowchart for the OCT apparatus with a tracking function using an SLO according to the embodiments of the present invention.

Next, as an operation procedure for the above-mentioned OCT apparatus with a tracking function using a line-scan SLO, an operation for extracting the characteristic points (also referred to as "characteristic images") is described with reference to a flowchart of FIG. 5. The operation procedure is performed in the same manner even when another fundus imaging apparatus is used.

First, based on an operation performed by the operator (manipulator) 311, in Step 701, alignment of an overall apparatus with respect to the eye 100 to be inspected is executed by presenting the fixation index. The fixation index display part 132 is used for the alignment. The fixation index presented by the fixation index display part 132 may have any shape, color, and behavior as long as the orientation of the eye 100 to be inspected can be fixed to a given direction and the fixation position can be selected. For example, the fixation index is realized by turning on an LED in a desired position of LEDs having an array structure or displaying an arbitrary shape on a liquid crystal display. After the line of sight of the eye 100 to be inspected is fixed to the fixation index, the alignment is started.

The alignment is performed by using an SLO image. The SLO image is displayed on the display 305 in real time while being continuously taken with high speed. Several tens of SLO images can be continuously acquired per second. While viewing the display 305, the operator 311 appropriately performs the alignment on the apparatus with respect to the eye 100 to be inspected. The alignment is completed when the operator 311 inputs the completion of the alignment through an input part (not shown), and the CPU 313 advances to Step 702 for template extraction.

When being instructed to perform the template extraction, the CPU 313 extracts a plurality of small areas having characteristics, that is, a plurality of characteristic points from an SLO image 401 of FIG. 3 being one fundus image among the continuously-acquired SLO images. With regard to the number of extracted areas, it is desired to select four small areas from the SLO image, but three small areas that do not exist in a straight line may be selected. Further, the small area having a characteristic, that is, the characteristic point may be a one-dimensional image being a one-dimensional line segment or a two-dimensional image.

In FIG. 3, areas 402, 403, 404, and 405 are the small areas having characteristics (characteristic points). The small area having a characteristic is hereinafter referred to as "template". When the templates are set, the CPU 313 advances to Step 703 to start acquiring the OCT image in parallel with the acquisition of the SLO image.

An OCT image taking position can be specified by a straight line drawn by the operator 311 within the SLO image displayed on the display 305. Alternatively, all images may be taken by scanning a range that appears in the SLO image with the OCT beam to form a three-dimensional OCT image. In any case, the range in which the OCT can be taken is limited to the range that appears in the SLO image.

When the OCT image taking is started, the CPU 313 advances to Step 704 for the pattern matching. The CPU 313 uses the extracted templates 402, 403, 404, and 405 to perform the pattern matching on the continuously-acquired SLO images in order. The pattern matching represents a processing for finding out places most similar to the templates 402, 403, 404, and 405 from within the image. The CPU 313 performs the pattern matching to thereby detect changes in positions of the templates 402, 403, 404, and 405. After detecting the change in the position of each of the templates by the pattern matching, the CPU 313 advances to Step 705 for calculation of a correction amount. The CPU 313 detects a movement of the fundus of the eye to be inspected by performing calculation based on the changes in the positions of the templates 402, 403, 404, and 405 detected by the pattern matching. After the calculation of a correction amount is finished, the CPU 313 advances to Step 706. The CPU 313 sends a driving instruction to a driving member 314 according to the detected movement, and moves the OCT X correction scanner 138 and the OCT Y correction scanner 137. The correction processing allows the OCT beam to be accurately applied to the position specified by the operator 311 so as to compensate the movement of the fundus of the eye to be inspected. At this time, the correction may be made by the OCT X scanner 104 and the OCT Y scanner 105. Alternatively, the correction may be shared by four scanners of the OCT X correction scanner 138 (309), the OCT Y correction scanner 137 (310), the OCT X scanner 104 (306), and the OCT Y scanner 105 (307). Those scanners function as a correcting unit for making a correction of an application position of the measuring beam onto the eye to be inspected together with the CPU 313. Further, at that time, those scanners function as a scanning unit for scanning the measuring beam over the eye to be inspected, and are adjusted by the CPU 313 to thereby carry out adjustment of the measuring beam.

In Step 707, the CPU 313 functions as a detecting unit for detecting a movement of the eye to be inspected, and determines whether or not an instruction to complete the image taking has been issued by the operator 311 through the input part (not shown). If the instruction to complete the image taking has been issued, the CPU 313 completes the image taking. If the instruction to complete the image taking has not been issued, the CPU 313 advances to Step 708.

In Step 708, the CPU 313 determines whether or not the position in which the fixation index display part 132 (312) presents the fixation index has been moved or changed. If determining that the fixation index has not been moved, the CPU 313 returns to Step 703. What appears in the SLO image is the fundus image being a partial plane image of the fundus. To take the image of a part other than the part of the initial alignment, the operator 311 needs to move the fixation index presented by the fixation index display part 132. When the fixation index is moved, the range that appears in the SLO image is caused to change. Therefore, this raises a possibility that the initially-acquired templates 402, 403, 404, and 405 may fall out of the range that appears in the SLO image.

If the CPU 313 determines in Step 708 that the fixation index presented by the fixation index display part 132 has been moved or changed, the CPU 313 advances to Step 709 to determine whether or not the respective templates 402, 403, 404, and 405 fall out depending on the direction for moving the fixation index presented by the fixation index display part 132 and a displacement amount being a movement amount, based on at least one of a positional relationship between the individual templates and a layout of the individual templates within the fundus image. This step corresponds to a determination step according to the present invention. At this time, even if a part of each of the templates is missing, the CPU 313 determines that the template has fallen out. In this embodiment, the CPU 313 is configured to function as a determining unit for determining whether or not the previously-extracted characteristic points are included in the SLO image being the fundus image newly acquired in the above-mentioned manner. The determination is performed based on a relationship between the displacement amount of the fixation index and the position of the characteristic points within the fundus image. If determining that all the existing templates 402, 403, 404, and 405 are remaining because the fixation index presented by the fixation index display part 132 has been moved by a small distance and there is no need to again extract the templates, the CPU 313 does not again perform the extraction and returns to Step 703 to perform tracking by using the existing templates 402, 403, 404, and 405.

If the CPU 313 determines in Step 709 that the existing templates 402, 403, 404, and 405 include a template that falls out of the SLO image acquired after the movement of the fixation index presented by the fixation index display part 132 and that at least one of those templates is not included in the new fundus image, the CPU 313 advances to Step 710. In Step 710, the CPU 313 reacquires templates, the number of which corresponds to the number of templates that fall out, from the SLO image acquired after the movement of the fixation index. In this embodiment, the CPU 313 is configured to function as an extracting unit or a second extracting unit for extracting new characteristic points from within the new SLO image.

At this time, the range for reacquiring the templates is limited to a remaining part of an SLO image 406 acquired after the movement of the fixation index except peripheries 407 and 408 of the templates 404 and 405, respectively, entirely remaining within the SLO image 406 acquired after the movement of the fixation index among the existing templates 402, 403, 404, and 405. In other words, coordinates of the characteristic points or the templates existing both before and after the movement of the fixation index are used to set a range for extracting new templates. That is, templates (referred to also as "second characteristic points" or "second characteristic images") are extracted from the range (referred to also as "range based on the changed presentation position") including at least a part of an image absent from the fundus image (first fundus image) taken before the presentation position of the fixation index is changed, within the fundus image (second fundus image) newly taken by changing the presentation position of the fixation index. In more detail, the peripheries 407 and 408 include the remaining templates and are set according to the displacement amount of the fixation index. Further, the peripheries 407 and 408 may have a range set to have a size of a predetermined scaling factor, for example, a magnification of nine times of the templates 404 and 405, respectively. In this case, the ranges of the peripheries 407 and 408 each have a quadrangular shape with the center coinciding with that of each of the templates 404 and 405, the X-axis direction length being three times as long as the X-axis direction length of each of the templates 404 and 405, and the Y-axis direction length being three times as long as the Y-axis direction length of each of the templates 404 and 405. In other words, a mode of setting the peripheries 407 and 408 under fixed conditions may be employed. In other words, it is preferred that the range for reacquiring the templates be set based on a relationship between the displacement amount of the fixation index and the positions within the fundus image of the characteristic points determined to be included in the new fundus image. If there is no template remaining in the new SLO image 406 among the existing templates 402, 403, 404, and 405, the entirety of the new SLO image 406 is set as the range for extracting new templates. Here, the CPU 313 functions as a setting unit for carrying out a setting step of setting the range for extracting new characteristic points. In a case of serving as the extracting unit or the secondly extracting unit to newly acquire a plurality of templates, the CPU 313 carries out an extracting step of dividing the above-mentioned range into a plurality of areas and extracting a template from each of the areas. Note that, in this embodiment, the characteristic points, the number of which is the same as the number of characteristic points that are no longer included in the new fundus image, are extracted again, which however may be changed according to the conditions.

That is, the CPU 313 serving as the extracting unit first extracts the first characteristic points from the first fundus image of the eye to be inspected. Subsequently, when the presentation position of the fixation index is changed, the second characteristic points are extracted from the range which is determined based on the presentation position of the fixation index after the change within the second fundus image of the eye to be inspected which is acquired at a time different from the acquisition of the first fundus image. In addition, the characteristic points included in the second fundus image among the first characteristic points and the second characteristic points are used to perform the pattern matching (or matching processing).

Further, as described above, the CPU 313 functions as the determining unit for determining whether or not each of the plurality of characteristic points extracted from the first fundus image is included in the second fundus image when the presentation position of the fixation index is changed, and also serves as the setting unit for setting the range which is determined based on the fixation index presentation position changed based on a determination result from the determining unit within the second fundus image. In addition, if the determining unit determines that at least one of the plurality of characteristic points is not included in the second fundus image, the setting unit in this case sets the range which is determined based on the changed presentation position within the second fundus image.

According to the above-mentioned configuration, the time period to reacquire the templates after the movement of the fixation index becomes shorter, and the tracking can be quickly performed on a new image-taking range. That is, the number of newly acquired templates can be minimized, which can shorten the time period.

Further, it is possible to acquire the tomographic image by correcting the movement of the eye to be inspected and to shorten the time period required until the acquisition.

Second Embodiment

In the first embodiment, the range for reacquiring templates after the movement of the fixation index is limited to the remaining part of the SLO image 406 acquired after the movement of the fixation index except the above-mentioned peripheries 407 and 408 of the templates 404 and 405, respectively, remaining within the SLO image 406 acquired after the movement of the fixation index among the existing templates 402, 403, 404, and 405. This is not essential conditions, and a configuration of a second embodiment may be employed.

The optical system including the SLO and the OCT apparatus is the same as that of the first embodiment. The method of performing the tracking of an OCT based on the SLO image is also the same. Only an algorithm for reacquiring the templates when the fixation index is moved is different.

The second embodiment is described with reference to a conceptual diagram of FIG. 4 illustrating a relationship between the SLO images and the templates. The templates used before the movement of the fixation index are the areas 402, 403, 404, and 405 extracted from the SLO image 401. Obtained after the movement of the fixation index is the SLO image 406, in which only the templates 404 and 405 remain among the existing templates 402, 403, 404, and 405. To compensate the fallen-out templates, the templates need to be reacquired. The range for acquiring new templates is limited to a range from a part that has newly appeared in the SLO image because of the movement of the fixation index presented by the fixation index display part 132 up to the templates 404 and 405 remaining among the existing templates. With reference to FIG. 4, new templates are extracted and acquired from a range between a dotted line 502 and a dotted line 504 and from a range between a dotted line 501 and a dotted line 503. The dotted lines 501 and 502 each represent a straight line existing on the most front side in a moving direction among straight lines to which line segments defining the sides of the templates remaining after the movement of the fixation index belong. The dotted lines 503 and 504 each represent a straight line to which the side located on the most front side in the moving direction belongs among the four sides of the SLO image that have appeared after the movement of the fixation index.

According to the above-mentioned configuration, in the same manner as in the first embodiment, the time period to reacquire the templates after the movement of the fixation index becomes shorter, and the tracking can be quickly performed on a new image-taking range.

Other Embodiments

Further, the present invention is realized by executing the following processing. That is, in the processing, software (a program) for implementing the functions of the above-mentioned embodiments is supplied to a system or an apparatus via a network or various storage mediums and is read and executed by a computer (or CPU, MPU, or the like) of the system or the apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-105402, filed Apr. 30, 2010, which is hereby incorporated by reference herein in its entirety.

What is claimed is:

1. An ophthalmologic apparatus comprising:
    a fixation index presenting unit configured to present a fixation index;
    a fundus image acquiring unit configured to acquire a first fundus image of an eye to be inspected and to acquire, after a presentation position of the fixation index is changed by the fixation index presenting unit, a second fundus image of the eye to be inspected;
    a first extracting unit configured to extract a plurality of characteristic images from the first fundus image;
    a determining unit configured to determine whether at least one of the plurality of characteristic images is not included in the second fundus image; and
    a second extracting unit configured, to extract at least one, differing from the plurality of characteristics images, characteristic image from a range in the second fundus image where the second fundus image is different from the first fundus image when it is determined by the determining unit that at least one of the plurality of characteristic images is not included in the second fundus image.

2. An ophthalmologic apparatus according to claim 1, wherein the is a range including at least a part of an image which is not included within the first fundus image but which is included within the second fundus image.

3. An ophthalmologic apparatus according to claim 1, wherein (a) at least one characteristic image included in the second fundus image among the exracted plurality of characteristic images, and (b) the extracted at least one characteristic image are used to perform pattern matching.

4. An ophthalmologic apparatus according to claim 1, wherein the determining unit determines whether or not each of the plurality of characteristic images extracted from the first fundus image is included in the second fundus image when the presentation position of the fixation index is changed.

5. An ophthalmologic apparatus according to claim 1, further comprising:
    a tomographic image acquiring unit configured to acquire a tomographic image of the eye to be inspected by causing interference between a return beam obtained by applying a measuring beam to the eye to be inspected and a reference beam;
    a detecting unit configured to detect a movement of the eye to be inspected based on the extracted at least one characteristic image; and
    a correcting unit configured to make a correction of an application position of the measuring beam onto the eye to be inspected based on the detected movement.

6. An ophthalmologic apparatus according to claim 5, further comprising a scanning unit configured to scan the measuring beam over the eye to be inspected,
    wherein the correcting unit makes the correction by adjusting the scanning unit.

7. An ophthalmologic method comprising the steps of:
    acquiring a first fundus image of an eye to be inspected, at a presentation position of a fixation index;
    extracting in a first extracting step first characteristic images from the first fundus image;
    acquiring a second fundus image of the eye, after the presentation position of the fixation index is changed; and
    determining whether at least one of the first characteristic images is not included in the second fundus image; and
    extracting in a second extracting step at least one second characteristic image, differing from the first characteristic images, from a range in the second fundus image where the second fundus image is different from the first fundus image when it is determined by the determining step that at least one of the first characteristic images is not included in the second fundus image.

8. An ophthalmologic method according to claim 7, wherein the second extracting step comprises extracting a number of images of the at least one second characteristic image, the number being the same as a number of the first characteristic images that are not included in the second fundus image.

9. An ophthalmologic method according to claim 7, wherein the step of determining is performed based on a relationship between a displacement amount of the fixation index and positions of the first characteristic images within the first fundus image.

10. An ophthalmologic method according to claim 7, wherein the determining step comprises determining the range based on a relationship between a displacement amount of the fixation index and positions within the fundus image of the first characteristic images determined to be included in the second fundus image.

11. An ophthalmologic method according to claim 7, wherein the first fundus image comprises a two-dimensional image.

12. An ophthalmologic method according to claim 7, wherein the first fundus image comprises one of (a) a one-dimensional line segment and (b) a two-dimensional image.

13. An ophthalmologic method according to claim 7, wherein each of the first characteristic images is determined to be included in the second fundus image in accordance with each of the first characteristic images being entirely included in the second fundus image.

14. A non-transitory tangible medium having recorded thereon a program for causing a computer to perform steps of the method according to claim 7.

15. An ophthalmologic method according to claim 7, wherein (a) at least one characteristic image included in the second fundus image among the first characteristic images, and (b) the at least one second characteristic image are used to perform pattern matching.

16. An ophthalmologic method according to claim 7, further comprising the steps of:
acquiring a tomographic image of the eye to be inspected by causing interference between a return beam obtained by applying a measuring beam to the eye to be inspected and a reference beam;
detecting a movement of the eye to be inspected based on the at least one second characteristic image; and
making a correction of an application position of the measuring beam onto the eye to be inspected based on the detected movement.

17. An ophthalmologic apparatus comprising:
a fixation index presenting unit configured to present a fixation index;
a fundus image acquiring unit configured to acquire a first fundus image of an eye to be inspected and to acquire, after a presentation position of the fixation index is changed by the fixation index presenting unit, a second fundus image of the eye to be inspected;
a first extracting unit configured to extract a plurality of characteristic images from the first fundus image;
a determining unit configured to determine a range based on the changed presentation position in the second fundus image when it is determined by the determining unit that at least one of the plurality of characteristic images is not included in the second fundus image; and
a second extracting unit configured to extract at least one characteristic image from the range.

18. An ophthalmologic method comprising the steps of:
acquiring a first fundus image of an eye to be inspected, at a presentation position of a fixation index;
extracting, in a first extracting step, first characteristic images from the first fundus image;
acquiring a second fundus image of the eye, after the presentation position of the fixation index is changed;
determining a range based on the changed presentation position in the second fundus image when it is determined by the determining step that at least one of the first characteristic images is not included in the second fundus image; and
extracting, in a second extracting step, at least one second characteristic image from the range.

19. A non-transitory tangible medium having recorded thereon a program for causing a computer to perform steps of the method according to claim 18.

20. An ophthalmologic apparatus according to claim 17, wherein (a) at least one characteristic image included in the second fundus image among the extracted plurality of characteristic images, and (b) the extracted at least one characteristic image are used to perform pattern matching.

21. An ophthalmologic method according to claim 18, wherein (a) at least one characteristic image included in the second fundus image among the first characteristic images, and (b) the at least one second characteristic image are used to perform pattern matching.

22. An ophthalmologic apparatus according to claim 17, further comprising: a tomographic image acquiring unit configured to acquire a tomographic image of the eye to be inspected by causing interference between a return beam obtained by applying a measuring beam to the eye to be inspected and a reference beam;
a detecting unit configured to detect a movement of the eye to be inspected based on the extracted at least one characteristic image; and
a correcting unit configured to make a correction of an application position of the measuring beam onto the eye to be inspected based on the detected movement.

23. An ophthalmologic method according to claim 18, further comprising the steps of:
acquiring a tomographic image of the eye to be inspected by causing interference between a return beam obtained by applying a measuring beam to the eye to be inspected and a reference beam;
detecting a movement of the eye to be inspected based on the at least one second characteristic image; and
making a correction of an application position of the measuring beam onto the eye to be inspected based on the detected movement.

24. An ophthalmologic apparatus comprising:
a fixation index presenting unit configured to present a fixation index;
a fundus image acquiring unit configured to acquire a first fundus image of an eye to be inspected and to acquire, after a presentation position of the fixation index is changed by the fixation index presenting unit, a second fundus image of the eye to be inspected;
a first extracting unit configured to extract a plurality of characteristic images from the first fundus image, as first characteristic images;
a determining unit configured to determine whether or not each of the plurality of characteristic images is included in the second fundus image;
a setting unit configured to set a range based on the changed presentation position in the second fundus image according to a determination result from the determining unit; and
a second extracting unit configured to extract at least one characteristic image from the range, as at least one second characteristic image.

25. An ophthalmologic method comprising the steps of:
acquiring a first fundus image of an eye to be inspected, at a presentation position of a fixation index;
extracting, in a first extracting step, first characteristic images from the first fundus image, as first characteristic images;
acquiring a second fundus image of the eye, after the presentation position of the fixation index is changed;
determining whether or not each of the plurality of characteristic images is included in the second fundus image;
setting a range based on the changed presentation position in the second fundus image according to a determination result of the determining step; and
extracting, in a second extracting step, at least one second characteristic image from the range, as at least one second characteristic image.

26. A non-transitory tangible medium having recorded thereon a program for causing a computer to perform steps of the method according to claim 25.

27. An ophthalmologic apparatus according to claim 24, wherein characteristic images included in the second fundus image among the first characteristic images, and the at least one second characteristic image extracted from the range are used to perform pattern matching.

28. An ophthalmologic method according to claim 25, wherein characteristic images included in the second fundus image among the first characteristic images, and the at least one second characteristic image extracted from the range are used to perform pattern matching.

29. An ophthalmologic apparatus according to claim 24, further comprising: a tomographic image acquiring unit configured to acquire a tomographic image of the eye to be inspected by causing interference between a return beam obtained by applying a measuring beam to the eye to be inspected and a reference beam;
a detecting unit configured to detect a movement of the eye to be inspected based on the extracted at least one characteristic image; and
a correcting unit configured to make a correction of an application position of the measuring beam onto the eye to be inspected based on the detected movement.

30. An ophthalmologic method according to claim 29, further comprising the steps of:
acquiring a tomographic image of the eye to be inspected by causing interference between a return beam obtained by applying a measuring beam to the eye to be inspected and a reference beam;
detecting a movement of the eye to be inspected based on the extracted at least one second characteristic image; and
making a correction of an application position of the measuring beam onto the eye to be inspected based on the detected movement.

31. An ophthalmologic apparatus comprising:
an extracting unit configured to extract a plurality of characteristic images from a first fundus image of an eye to be inspected;
a fixation index presenting unit configured to present a fixation index;
an acquiring unit configured to acquire, when a presentation position of the fixation index is changed by the fixation index presenting unit, a second fundus image of the eye to be inspected; and
a determining unit configured to determine whether at least one of the plurality of characteristic images is not included in the second fundus image and to determine at least one characteristic image from the plurality of characteristic images in a range of the fundus that can be observed based on the changed presentation position within the second fundus image.

32. An ophthalmologic method comprising the steps of:
extracting a plurality of characteristic images from a first fundus image of an eye to be inspected;
presenting a fixation index; acquiring, when a presentation position of the fixation index is changed, a second fundus image of the eye to be inspected;
determining whether at least one of the plurality of characteristic images is not included in the second fundus image; and
determining at least one characteristic image from the plurality of characteristic images in a range of the fundus that can be observed based on the changed presentation position within the second fundus image.

33. A non-transitory tangible medium having recorded thereon a program for causing a computer to perform steps of the method according to claim 32.

* * * * *